US011188285B2

(12) United States Patent
Kehat et al.

(10) Patent No.: US 11,188,285 B2
(45) Date of Patent: Nov. 30, 2021

(54) INTELLIGENT DISPLAY

(71) Applicant: COVIDIEN LP, Mansfield, MA (US)

(72) Inventors: Israel Kehat, Ramat Hasharon (IL); Eyal Klein, Herzliya (IL); Benjamin Greenburg, Hod Hasharon (IL); Dorian Averbuch, Ramat Hasharon (IL)

(73) Assignee: COVIDIEN LP, Mansfield, MA (US)

( * ) Notice: Subject to any disclaimer, the term of this patent is extended or adjusted under 35 U.S.C. 154(b) by 105 days.

(21) Appl. No.: 14/754,058

(22) Filed: Jun. 29, 2015

(65) Prior Publication Data

US 2016/0000517 A1   Jan. 7, 2016

Related U.S. Application Data

(60) Provisional application No. 62/020,238, filed on Jul. 2, 2014.

(51) Int. Cl.
*G06F 3/14* (2006.01)
*A61B 1/267* (2006.01)
(Continued)

(52) U.S. Cl.
CPC .............. *G06F 3/14* (2013.01); *A61B 1/0005* (2013.01); *A61B 1/2676* (2013.01); *A61B 5/066* (2013.01);
(Continued)

(58) Field of Classification Search
CPC .. G06F 3/00; A61B 34/00; A61B 1/00; A61B 5/00; A61B 2090/00; A61B 2034/00; A61B 34/20
See application file for complete search history.

(56) References Cited

U.S. PATENT DOCUMENTS 5,605,531 A * 2/1997 Lane ..................... A61B 1/042
                                                           348/74
6,049,622 A   4/2000 Robb et al.
(Continued)

FOREIGN PATENT DOCUMENTS

CN   101681514 A   3/2010
CN   102470014 A   5/2012
(Continued)

OTHER PUBLICATIONS

Supplementary European Search Report dated Mar. 1, 2018 and issued in corresponding European Patent Application No. 15814669.
(Continued)

*Primary Examiner* — Sean D Mattson
(74) *Attorney, Agent, or Firm* — Carter, DeLuca & Farrell LLP

(57) ABSTRACT

A medical image display apparatus for displaying medical images of a lung on a screen includes a network interface receiving positional information of a navigation instrument from a position sensor of the navigation instrument, a video stream from an optical sensor of the navigation instrument, and medical images from an imaging device, a memory storing a plurality of medical images and instructions, a processor executing the instructions, and a display dynamically displaying images on the screen. The instructions, when executed by the processor, cause the medical image display apparatus to determine whether status information indicates a pathway reviewing mode, a target management mode, or a navigation mode. The instructions, when executed by the processor, further cause the display to dynamically select and update images, which are displayed on the screen, among the plurality of medical images based on the positional information of the navigation instrument and status information.

10 Claims, 7 Drawing Sheets

(51) Int. Cl.
    *A61B 5/06*        (2006.01)
    *G06T 11/60*     (2006.01)
    *A61B 34/00*     (2016.01)
    *A61B 34/20*     (2016.01)
    *A61B 1/00*       (2006.01)
    *A61B 5/00*       (2006.01)
    *A61B 90/00*     (2016.01)

(52) U.S. Cl.
    CPC .............. *A61B 34/20* (2016.02); *A61B 34/25* (2016.02); *G06T 11/60* (2013.01); *A61B 5/0013* (2013.01); *A61B 5/7425* (2013.01); *A61B 2034/2051* (2016.02); *A61B 2034/2065* (2016.02); *A61B 2090/364* (2016.02); *A61B 2090/367* (2016.02); *A61B 2090/374* (2016.02); *A61B 2090/3762* (2016.02); *A61B 2560/0475* (2013.01); *G06T 2211/412* (2013.01); *G06T 2211/428* (2013.01); *G09G 2380/08* (2013.01)

(56) References Cited

U.S. PATENT DOCUMENTS

| | | | |
|---|---|---|---|
| 6,343,936 B1 | 2/2002 | Kaufman et al. | |
| 6,928,314 B1* | 8/2005 | Johnson | G06T 15/08 128/920 |
| 7,356,367 B2 | 4/2008 | Liang et al. | |
| 7,599,730 B2 | 10/2009 | Hunter et al. | |
| 8,046,052 B2 | 10/2011 | Verard et al. | |
| 8,199,984 B2 | 6/2012 | Mori et al. | |
| 8,217,966 B2 | 7/2012 | Fram et al. | |
| 8,248,413 B2 | 8/2012 | Gattani et al. | |
| 8,467,853 B2 | 6/2013 | Hunter et al. | |
| 8,610,746 B2 | 12/2013 | Fram et al. | |
| 8,696,548 B2 | 4/2014 | Gilboa | |
| 8,992,232 B2 | 3/2015 | Berry et al. | |
| 2003/0114730 A1* | 6/2003 | Hale | A61B 1/00039 600/114 |
| 2005/0020878 A1* | 1/2005 | Ohnishi | A61B 1/00009 600/117 |
| 2005/0107679 A1* | 5/2005 | Geiger | G06T 19/003 600/407 |
| 2005/0113812 A1 | 5/2005 | Viswanathan et al. | |
| 2006/0025679 A1* | 2/2006 | Viswanathan | A61B 34/20 600/424 |
| 2007/0003124 A1* | 1/2007 | Wood | A61B 6/032 382/131 |
| 2007/0032720 A1* | 2/2007 | Koivukangas | A61B 5/055 600/407 |
| 2008/0071143 A1* | 3/2008 | Gattani | A61B 1/00009 600/117 |
| 2008/0118135 A1 | 5/2008 | Averbuch et al. | |
| 2008/0207997 A1* | 8/2008 | Higgins | A61B 1/00009 600/114 |
| 2008/0300478 A1* | 12/2008 | Zuhars | A61B 5/062 600/407 |
| 2009/0063118 A1 | 3/2009 | Dachille et al. | |
| 2009/0227861 A1 | 9/2009 | Ganatra et al. | |
| 2010/0008555 A1* | 1/2010 | Trumer | A61B 6/12 382/131 |
| 2010/0249507 A1* | 9/2010 | Prisco | A61B 1/00009 600/117 |
| 2011/0187707 A1* | 8/2011 | Kaufman | A61B 1/00009 345/419 |
| 2012/0022546 A1* | 1/2012 | Hubschman | A61F 9/00736 606/107 |
| 2012/0046521 A1* | 2/2012 | Hunter | A61B 1/2676 600/104 |
| 2012/0089014 A1 | 4/2012 | Sabczynski et al. | |
| 2012/0207365 A1* | 8/2012 | Verstraeten | G16H 50/50 382/128 |
| 2012/0249546 A1* | 10/2012 | Tschirren | G06T 19/00 345/419 |
| 2012/0287238 A1 | 11/2012 | Onishi et al. | |
| 2013/0208955 A1* | 8/2013 | Zhao | G06F 19/321 382/128 |
| 2014/0051986 A1 | 2/2014 | Zhao et al. | |
| 2014/0275952 A1* | 9/2014 | Monroe | G06T 19/00 600/407 |
| 2014/0344742 A1* | 11/2014 | Wiemker | G06T 19/003 715/771 |
| 2016/0183841 A1* | 6/2016 | Duindam | A61B 17/34 600/424 |
| 2017/0035517 A1* | 2/2017 | Geri | G06T 19/20 |

FOREIGN PATENT DOCUMENTS

| | | |
|---|---|---|
| CN | 103068294 A | 4/2013 |
| JP | 2010510815 A | 4/2010 |
| JP | 2010172350 A | 8/2010 |
| JP | 2010528750 A | 8/2010 |
| WO | 2008125910 A2 | 10/2008 |
| WO | 2008149274 A1 | 12/2008 |
| WO | 2009102984 A2 | 8/2009 |
| WO | 2010086909 A1 | 8/2010 |
| WO | 2012101888 A1 | 8/2012 |
| WO | 2015023665 A1 | 2/2015 |

OTHER PUBLICATIONS

Examination Report issued by the Australian Patent Office dated Mar. 22, 2019 in corresponding Australian Patent Application No. 2015284290.

Examination Report issued by the Australian Intellectual Property Office dated Jul. 2, 2019 in corresponding Australian Patent Application No. 2015284290.

Notice of Reasons for Rejection issued by the Japanese Patent Office dated Mar. 4, 2019 in corresponding Japanese Patent Application No. 2016-575495, with English translation.

Notification of the First Office Action issued by the China National Intellectual Property Administration dated Jun. 24, 2019 in corresponding Chinese Patent Application No. 201580042951.8, with English translation.

Third Office Action issued in corresponding Chinese Appl. No. 201580042951.8 dated Aug. 13, 2020 (11 pages) together with English Language translation retrieved from the Global Dossier (18 pages).

European Examination Report issued in corresponding application EP 15814669.6 dated May 10, 2021 (4 pages).

* cited by examiner

INTELLIGENT DISPLAY

CROSS REFERENCE TO RELATED APPLICATIONS

The present application claims the benefit of and priority to U.S. Provisional Patent Application Ser. No. 62/020,238 filed on Jul. 2, 2014, the entire contents of which are incorporated herein by reference.

BACKGROUND

Technical Field

The present disclosure relates to systems for displaying medical images in a dynamic and changing manner. More particularly, the present disclosure relates to systems that dynamically display medical images based on a position, a status of a navigation instrument, and functions to achieve at each point in time.

Discussion of Related Art

Visualization techniques have been rapidly growing in medical areas. In particular, visualization techniques has helped minimizing a size of an incision or non-invasively treating diseases of a patient in surgeries and non-invasively navigating inside of patients to identify and treat target lesions. However, visualization may also pose unexpected risks when incorrect information is displayed. Further, when improper information is displayed, clinicians may have difficult times to interpret the displayed information.

Clinicians need to obtain correct and appropriate information in a dynamic manner depending on procedures and/or functions that the clinicians want to achieve while using medical devices. When medical devices are capable of displaying correct and appropriate information under the circumstances, clinicians need less training. Also, when settings are automatically adjusted to display information under circumstances, clinicians and staff members can experience faster and easier use. Automatic adjustments are more beneficial when clinicians or staff members do not regularly use the medical device.

SUMMARY

In an embodiment, the present disclosure discloses a medical image display apparatus for displaying medical images of a lung on a screen. The medical image display apparatus includes a network interface configured to receive positional information of a navigation instrument from a position sensor of the navigation instrument, a video stream from an optical sensor of the navigation instrument, and medical images from an imaging device, a memory storing a plurality of medical images and instructions, a processor configured to execute the instructions, and a display configured to dynamically display images on the screen. The instructions, when executed by the processor, cause the medical image display apparatus to determine whether status information indicates a pathway reviewing mode, a target management mode, or a navigation mode. The instructions, when executed by the processor, further cause the display to dynamically select and update images, which are displayed on the screen, among the plurality of medical images based on the positional information of the navigation instrument and status information.

In an aspect, the navigation instrument is an endoscopic instrument.

In another aspect, the plurality of medical images are selected from the group consisting of sagittal, coronal, or axial images, a three-dimensional (3D) map of the lung, a target, a pathway plan to the target, virtual bronchoscopic video images, live bronchoscopic video images, a maximum intensity projection image, a 3D CT image, a distal tip of the navigation instrument, and any combination thereof. The sagittal, coronal, or axial images are captured by computed tomography, fluoroscope, computer aided tomography, positron emission tomography, or magnetic resonance imaging. A displayed image is a composite image, in which a first image of the lung obtained from a first imaging method is overlaid with a second image obtained from another imaging method.

In an aspect, the portion is the target, the first image is captured by computed tomography, and the second image is captured by fluoroscope. The display displays two or more images synchronously corresponding to changes in the positional information.

In another aspect, when the target is displayed in the 3D map, a sagittal image, a coronal image, and/or an axial image are selected and displayed based on positional information of the target. Changes in the positional information indicate movements of the position sensor of the navigation instrument in the lung.

In yet another aspect, the axial, coronal, and sagittal images are displayed based on the positional information of the position sensor of the navigation instrument. Each of the axial, coronal, and sagittal images is controlled by a control which includes zooming and panning.

In yet another aspect, the 3D map is displayed with an orientation indicator which shows an orientation of the 3D map.

In yet another aspect, the display displays the live bronchoscopic video images, when the positional information indicates the position sensor does not pass a threshold position, and the display removes the live bronchoscopic video images and displays the virtual bronchoscopic video images when the positional information indicates the position sensor passes the threshold position.

In yet another aspect, the display displays a last received image when the status information indicates that no live bronchoscopic video images are received from the navigation instrument in the navigation mode.

In yet still another aspect, the display automatically orients the 3D map to show a current position of the position sensor in the 3D map with sufficient clarity.

In another embodiment, the present disclosure discloses a medical image display system for displaying medical images on a screen. The medical image display system includes an imaging device configured to captures images of a patient, a navigation instrument configured to navigate inside of the patient, to transmit positional information obtained by a position sensor and video stream obtained by an optical sensor, and an apparatus, which includes a network interface configured to receive the positional information and the video stream from the navigation instrument and the captured images from the imaging device, a processor configured to execute instructions, a memory storing a plurality of medical images and the instructions, and a display configured to display images on the screen. The instructions, when executed by the processor, cause the apparatus to determine a status of the navigation instrument, which indicates whether the navigation instrument transmits the positional information and the video stream, and cause the display to dynamically select and update images, which are displayed on the screen, among a plurality of images based on the positional information and status information of the navigation instrument.

In yet another embodiment, the present disclosure discloses a method for dynamically displaying medical images of a lung on a display of a display device, which stores slice images of the lung, three-dimensional (3D) map of the lung, and a pathway plan to a target. The method includes determining whether status information of the display device indicates a pathway reviewing mode, a navigation mode, or a target management mode, receiving positional information from a navigation instrument, which indicates a position of a position sensor of the navigation instrument navigating the lung, and displaying medical images based on the determined status information and the positional information. The displayed medical images include the 3D map and virtual bronchoscopic video images, which are overlaid with the pathway plan and the target, when the determined status information is the pathway reviewing mode. The displayed medical images include the 3D map, the virtual or live bronchoscopic video images, and slice images, all of which synchronously track the positional of the position sensor, when the determined status information is the navigation mode. The displayed medical images include three slice images, which are taken from three independent directions, and a maximum intensity projection image displaying the target, when the determined status information is the target management mode. When one image is panned or zoomed in the navigation mode, all images and the 3D map are synchronously panned or zoomed correspondingly.

Any of the above aspects and embodiments of the present disclosure may be combined without departing from the scope of the present disclosure.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which.

DETAILED DESCRIPTION

The present disclosure is related to systems and methods for dynamically displaying medical images on a screen. The systems display update and adjust appropriate information using visual, audible, and tactile information based on a position of an endoscopic device's position inside of a patient. Dynamically and automatically changing images on the screen based on a location of the endoscopic device and status information promotes ease of use of the display systems, and reduces the need for clinician interaction the adjust and change the display.

Figure 1:
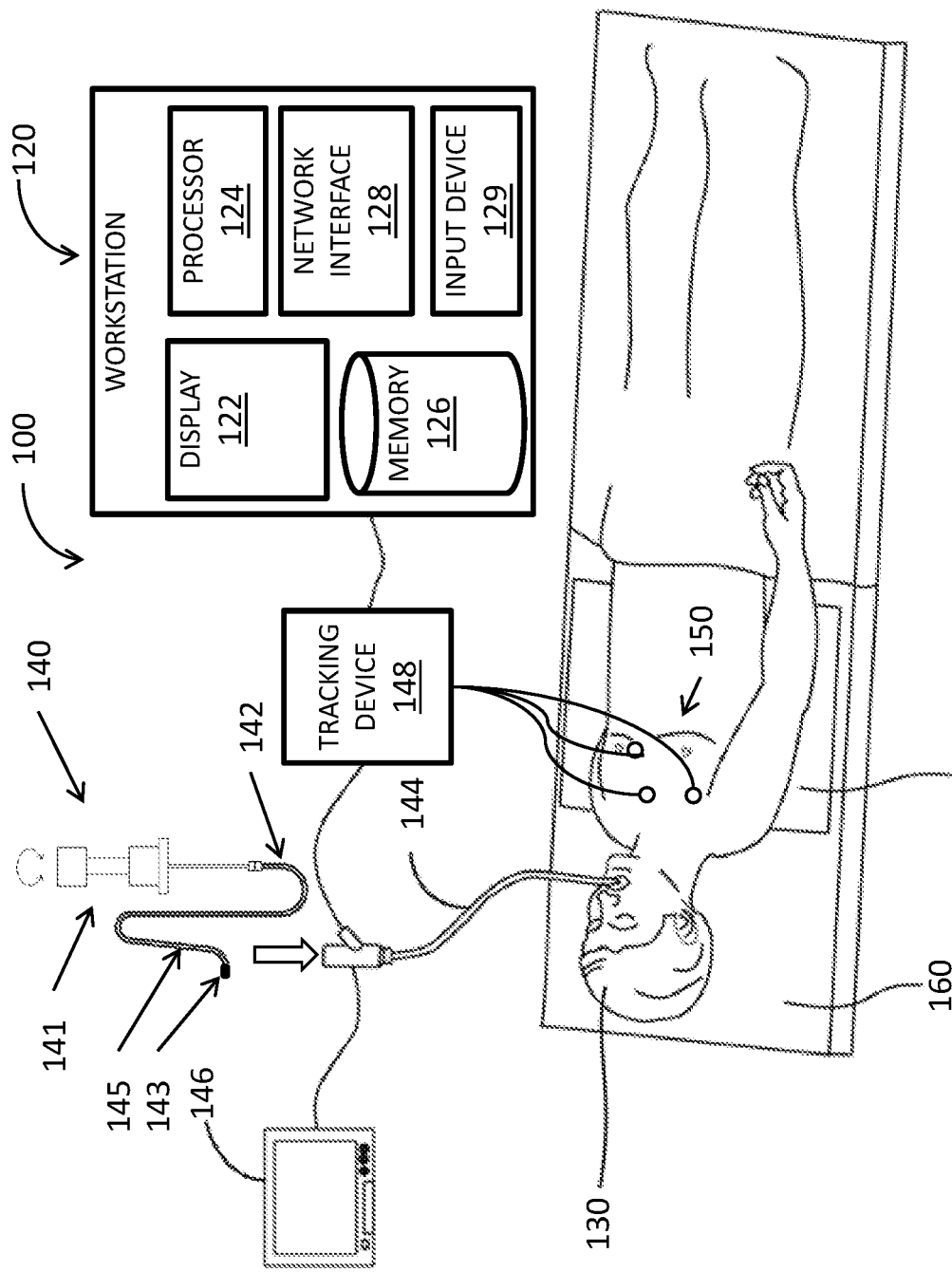
FIG. 1 is a perspective view of a system for dynamically displaying medical images on a screen in accordance with an embodiment of the present disclosure.

FIG. 1 shows an endoscopic navigation system 100 for non-invasively visualizing inside of a patient's chest and dynamically displaying medical images and processed images on a screen. In particular, the endoscopic navigation system 100 includes a workstation 120 and a navigation instrument 140. The workstation 120 includes a display 122, one or more processors 124, memory 126, a network interface 128, and an input device 129.

The navigation instrument 140 includes a catheter 142, which can be inserted into the working channel of a bronchoscope 144. A monitoring device 146 displays images generated by the bronchoscope 144. A handle 141 at the proximal end of the navigation instrument 140 is operatively connected to the catheter 142 enables navigation of the catheter 142 into areas of the patient which are too narrow for the bronchoscope 144 to navigate. The navigation instrument 140 may include a sensor 143. The sensor 143 may be integrally formed in the catheter 142, or may be formed on a locatable guide (LG) 145 insertable through a lumen of the catheter 142. When using the LG 145 during navigation, upon reaching a target, the LG 145 may be removed from the lumen in the catheter 142 leaving the catheter 142. In this way, when other surgical operations (e.g., biopsy, ablation, sealing, or cauterization) are needed, a surgical tool corresponding to the surgical operation may be inserted through the catheter 142 to reach the target.

The endoscopic navigation system 100 further includes a surgical table 160. An electromagnetic (EM) field generator 165 is associated with the surgical table 160 (e.g., placed under, integrated with, or placed on top of, but under the patient 130) and may be used to help identify a location of the sensor 143 within the EM field (not shown) generated by EM field generator 165.

The endoscopic navigation system 100 may also include a tracking device 148 and reference sensors 150 placed on the patient 130. The navigation instrument 140 is operatively coupled to the tracking device 148 via bronchoscope 144 through a wired connection or wireless connection (not shown). The reference sensors 150 sense the electromagnetic field generated by the EM field generator 165 and sense a movement pattern of the chest due to the patient's breathing. The reference sensors 150 may compensate the patient's breathing pattern to more assist in identifying the location of the sensor 143 within the electromagnetic field.

The tracking device 148 receives the positional information from the sensor 143 associated with the navigation instrument 140 and the reference sensors 150 to identify the location of the sensor 143 within the patient, and associate that position with 2-dimensional images and 3-dimensional maps to enable navigation of the navigation instrument 140 within the patient 130.

The positional information is identified in the coordinate system of the 3D map so that the workstation 120 may be able to display the position of the sensor 143 in the 3D map. Displaying the 3D map and slice images are described further in detail below.

The one or more processors 124 execute computer-executable instructions. The processors 124 may perform image-processing functions so that a 3D map of the lung of the patient 130 can be generated from imported Digital Image and Communication in Medicine (DICOM) images. The display 122 may display two dimensional (2D) images or a three dimensional (3D) map of the portion of the patient 130. The processor 124 may process the sensed positional information from the sensor 143 to identify the position of the sensor 143, and through a registration process provide an indication of the location of the sensor 143 in the 2D images or 3D map. The 2D images and 3D map may also be used to locate and identify a lesion or tumor as a point of interest for example for biopsy or treatment and generate a pathway to reach that target and enable navigation to the target inside the patient 130.

The memory 126 stores data and programs. In an aspect, data may be DICOM images, 3D maps, or any other related data such as patient's medical records, prescriptions, and history of the patient's diseases, and programs may be navigation and pathway planning software to provide guidance to the clinician and to provide a representation of the pathway on the 3D map and 2D images. Examples of programs which may be stored in the memory include the ILOGIC® navigation planning and procedure suites sold by Covidien LP. Details of the planning suite can be found in U.S. patent application Ser. Nos. 13/838,805, 13/838,997, and 13/839,224, filed on Mar. 15, 2013, and entitled "Pathway Planning System and Method," and of the procedure suite can be found in U.S. Provisional Patent Application Ser. No. 62/020,240 entitled "System And Method For Navigating Within The Lung," filed on Jul. 2, 2014, by Brown et al., all of which are filed by Covidien LP and the entire contents of which are incorporated herein by reference.

FIGS. 2-5 illustrate various windows that the workstation 120 can present on the display 122 in accordance with embodiments of the present disclosure. The display 122 may present specific windows based on a mode of operation of the endoscopic navigation system 100, these modes may include a target management mode, a pathway planning mode, a navigation mode, and others as detailed herein.

Figure 2:
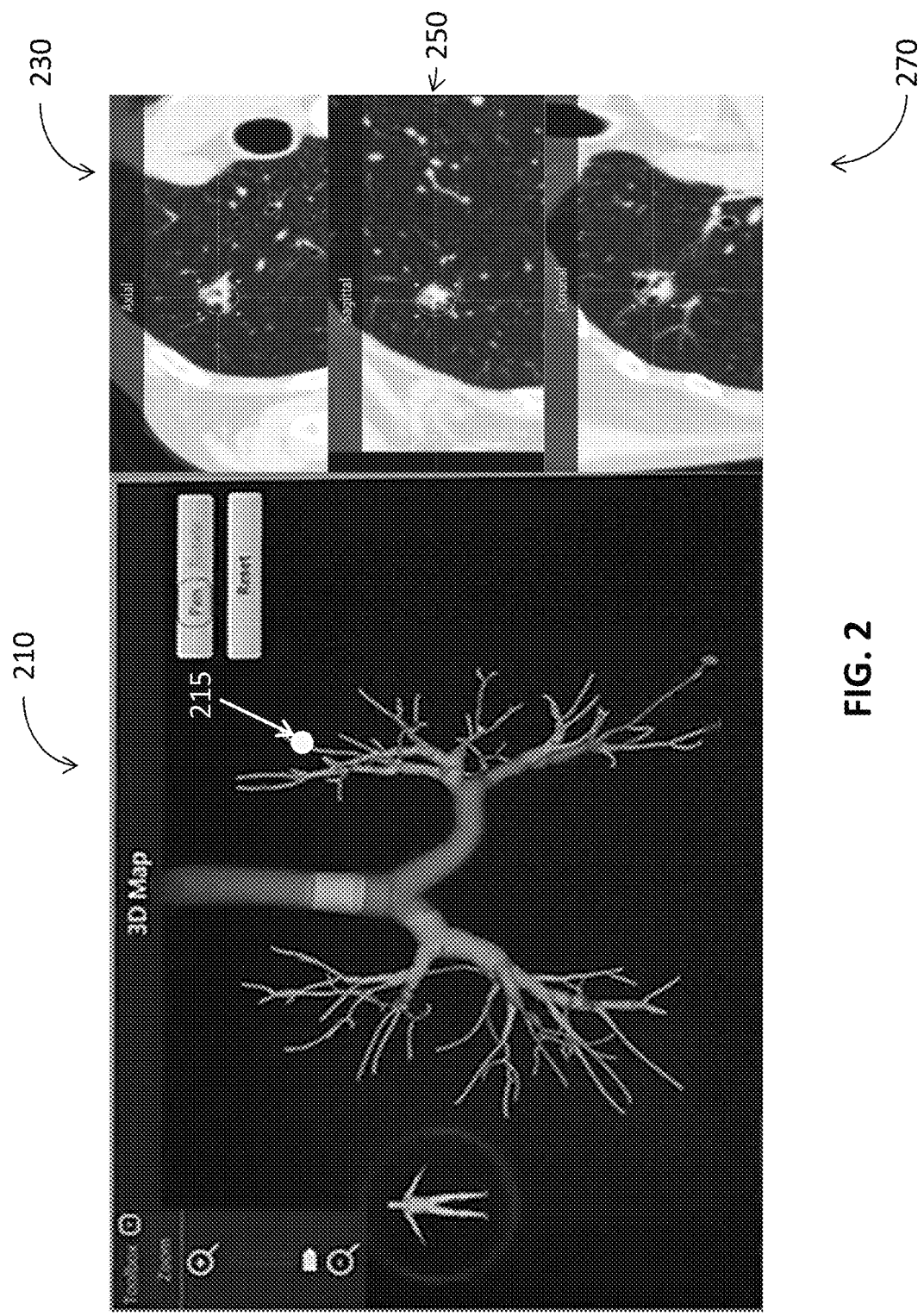
FIGS. 2-5 are graphical illustrations of images dynamically displayed on the screen of the system of FIG. 1 in accordance with an embodiment of the present disclosure.

FIG. 2 illustrates the target management mode in accordance with embodiments of the present disclosure. After a target is identified, clinicians may review and manage to prioritize or confirm a location or size of each target. The target management mode may include a 3D map window 210 and three windows including the axial view window 230, the coronal view window 250, and the sagittal view window 270. The 3D map window 210 may be located in the left side and show a target 215. The target 215 is not displayed proportionally in size but displayed to bring clinicians' attention to the location thereof. Three windows 230-270 are selected based on the location of the target 215.

In an aspect, the display 122 may display all identified targets in the 3D map window 210. When a target is selected by a clinician's finger or by a pointing device, three windows 230-270 are automatically displayed showing the axial, sagittal, and coronal images intersecting each other at the location of the selected target. Further, the selected target may be displayed in a different color or shape so that the selected target can be distinguished from other non-selected targets in the 3D map window 210. The 3D map window 210 and the three windows 230-270 may be synchronized based on the selected target. The size and location information of the selected target may be compared and identified with information displayed in the three windows 230-270. A clinician may revise or correct the size and location information of the selected target at the spot.

In another aspect, targets already displayed in the 3D map window 210 may be removed and a new target may be added in the target management mode. For example, when a target is selected and corresponding menu is displayed, removing a target may be selected. Then the target is removed from the 3D map window 210 and corresponding slice images are not displayed on the right side of the target management window. Or when a new target is added, the new target is displayed in the 3D map window 210 and corresponding three slice images are also displayed in the right side of the target management window in a stacked form. As described above, these windows 210, 230, 250, and 270 may be manually controlled to change their sizes and locations as clinician's preferences.

In an aspect, when a target is not displayed clearly because of the location of a target, the 3D map window 210 may be automatically switched to a 3D map dynamic window, which can be rotated, panned, or zoomed. The 3D map dynamic window may be automatically rotated, panned, or zoomed in such a way that the target can be displayed with clarity. In an aspect, the displayed windows of FIG. 2 may be displayed in a navigation phase to show where a next target may be when a biopsy tool is taken.

Figure 3:
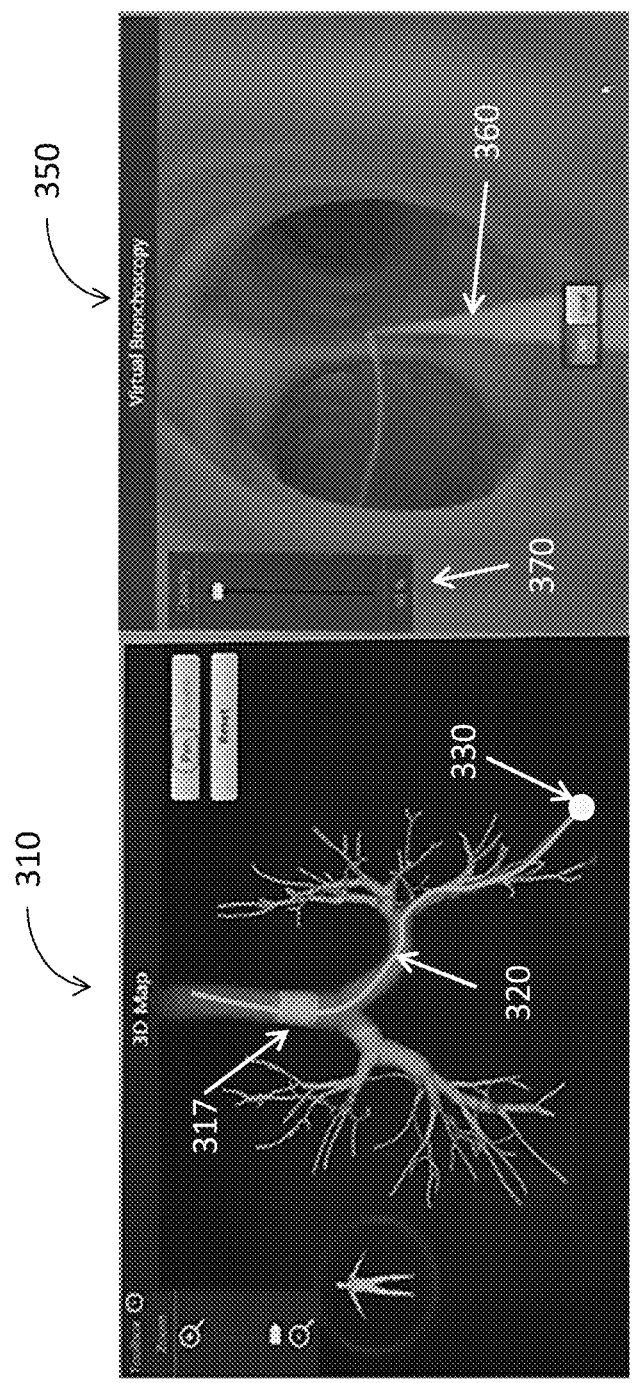

When a target is identified and a pathway is identified by the workstation 120, a clinician may want to review the pathway in a navigation review mode. FIG. 3 illustrates the navigation review mode of the planning phase, in which the workstation 120 shows a 3D map window 310 and a virtual bronchoscopy window 350 on the screen of the display 122 in accordance with embodiments of the present disclosure. The 3D map window 310 shows the 3D map and the virtual bronchoscopy window 350 shows virtual bronchoscopic video images. The 3D map window 310 visibly displays and overlays a pathway 320 to a target 330 and a current position indicator 317. In the navigation review mode, the display 122 always shows the virtual bronchoscopy window 350 as a fly-through view from the trachea to the target 330 is presented.

The virtual bronchoscopy window 350 also shows a pathway 360 toward the target 330 for a review. The current position indicator 317 moves in the 3D map window 310 based on and in accordance with the current position shown in the virtual bronchoscopy window 350. In an aspect, the pathway 360 or 320 may not be displayed based on a display option that a clinician may set between showing the pathway and not showing the pathway.

The virtual bronchoscopy window 350 includes a slider 370 for opacity. By moving the slider 370, opacity of the virtual bronchoscopic video images may be changing from opaque to transparent. However, an opacity status of the virtual bronchoscopy is not synchronized with the 3D map shown in the 3D map window 310.

Figure 4A:
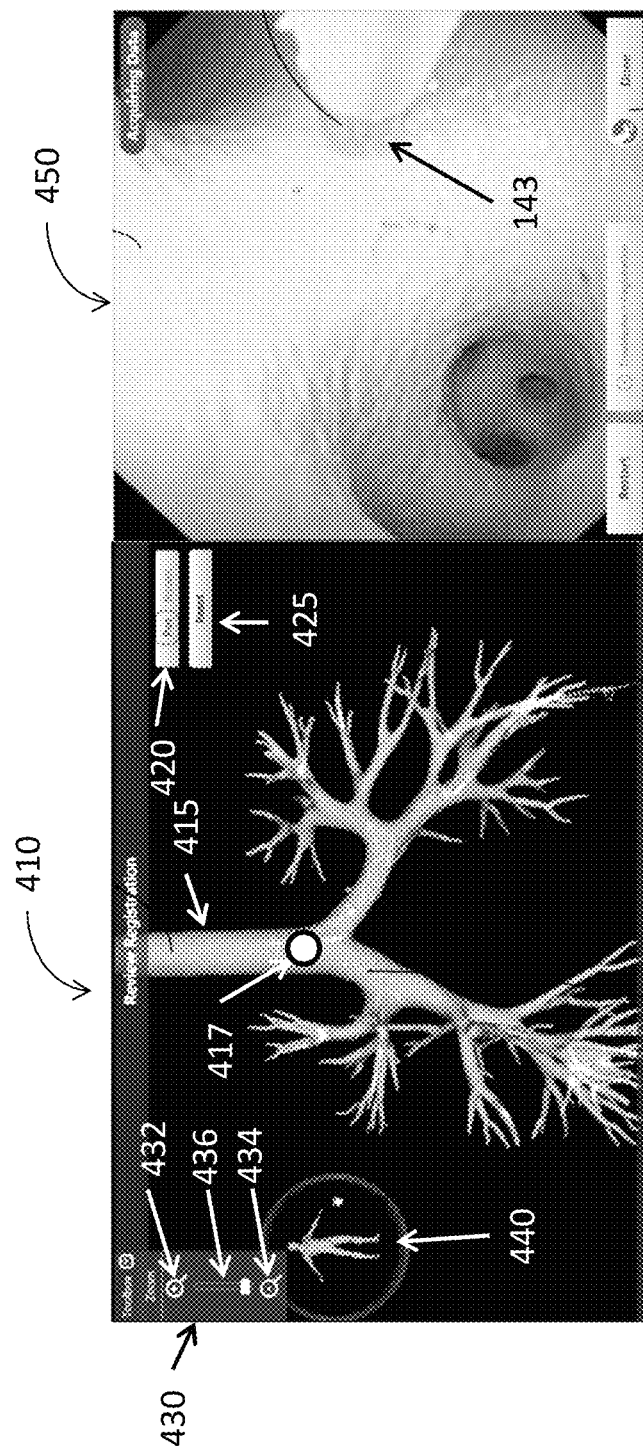
Figure 4B:
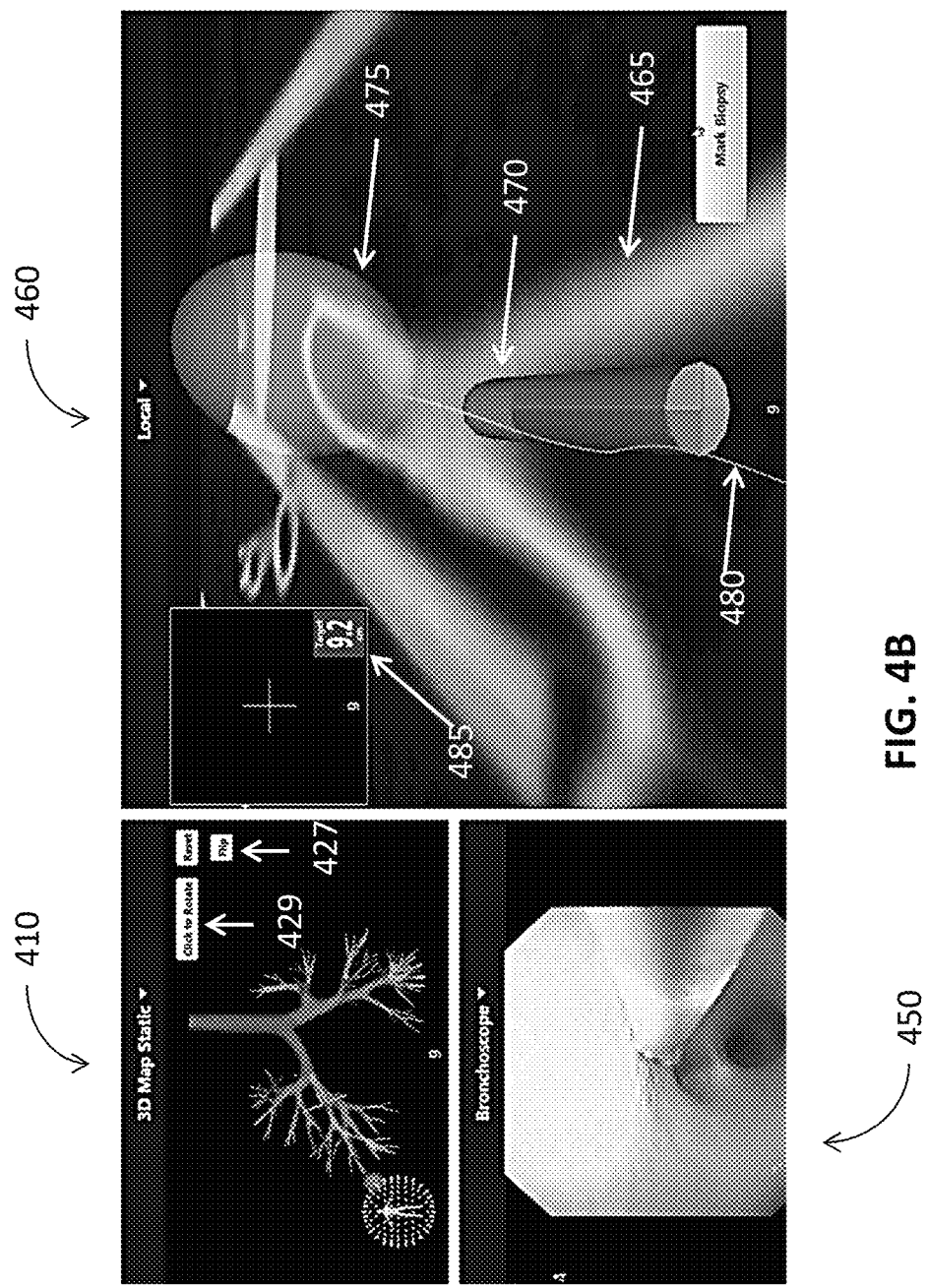

FIGS. 4A and 4B illustrate windows displayed during a navigation mode, which includes a central mode and a peripheral navigation mode in accordance with embodiments of the present disclosure. In the central mode, the workstation 120 may display the 3D map window 410 and live bronchoscopy window 450 as shown in FIG. 4A.

The 3D map window 410 displays a 3D map of the airways of a patient and the live bronchoscopy window 450 displays live bronchoscopic video images received by an optical sensor positioned at the distal end of the bronchoscope 144. In a case when a target is at a central airway of the lung (e.g., the trachea or the primary bronchus), the bronchoscope can reach the target and the live bronchoscopy window 450 can display the live bronchoscopic video images and the pathway to the target.

The 3D map window 410 displays a 3D map 415 of the lung and a current position indicator 417 indicating a current position of the sensor 143 of the LG 145 of the catheter 142. As the sensor 143 navigates the lung toward a target, the current position indicator 417 moves in the 3D map 415 to a position that corresponds to the actual position of the sensor 143 in the lung. For example, the sensor 143 is proximate a branching position of the lung in the live bronchoscopy window 450 and the current position indicator 417 is also proximate a branching position of the 3D map 415 as shown in FIG. 4A. In other words, the live bronchoscopy window 450 and the 3D map window 410 synchronize the current position of the sensor 143 via the current position indicator 417 in the 3D map 415.

The 3D map window 410 also shows a pan/zoom selector 420 and a reset button 425. When a pan is selected in the pan/zoom selector 420, the 3D map 415 can be panned. For example, when the zoom is selected, the 3D map 415 can be zoomed. The 3D map window 410 also shows an orientation indicator 440 in a form of a human body. The orientation indicator 440 shows orientation of the 3D map 415 when the 3D map is panned and/or zoomed. The pan and the rotate functions are activated when the pan function or the zoom function is selected in the pan/zoom selector 420. Clinicians may pan or zoom in or out the 3D map 415 by clicking and dragging the 3D map 415 or the orientation indicator 440 to the right, left, up, and down or in any direction.

In an embodiment, the 3D map 415 may be rotated around the center of the 3D map window 410 in any direction by clicking and dragging, or in other words in a direction of combination of pan and zoom. In another embodiment, the 3D map 415 may be panned around the current position of the current position indicator 417. Both of the 3D map 415 and the orientation indicator 440 synchronously pan and zoom. In a case when the reset button 425 is pressed, the 3D map 415 is rotated to a default orientation by automatically panning and zooming based on the position of the current position indicator 417. The default orientation may be the anterior up position or may be changed to the posterior up position based on the setting of the display 122.

In another embodiment, the 3D map 415 may be automatically panned or zoomed to clearly show the position of the current position indicator 417. For example, when the current position indicator 417 is positioned in an anterior lobe of the 3D map 415 and cannot be clearly shown without zooming or panning the 3D map 415, the 3D map 415 may be automatically rotated and/or zoomed to clearly show the current position on the screen based on the position of the current position indicator 417 in the 3D map 415.

In still another embodiment, the reset button 425 may activate automatic pan and/or zoom based on the position of the current position indicator 417 in the 3D map 415, and the pan/zoom selector 420 may deactivate the automatic pan and/or zoom and activate the manual pan or zoom. In this way, the display 122 helps clinicians view the actual position of the sensor 143 in the lung, which is synchronized with the position of the current position indicator 417 in the 3D map 415, without touching or manipulating the display 122. Also, clinicians are able to manually rotate the 3D map to check the location of the targets and lung structures near the position of the current position indicator 417.

The 3D map window 410 also shows a zoom tool 430, which includes a zoom-in button 432, a zoom-out button 434, and a zoom slider 436. The zoom-in button 432 zooms in around the position of the current position indicator 417 and the zoom-out button 434 zooms out around the position of the current position. The zoom slider 436 may be used to zoom-in and out by moving a slider up and down, respectively. In an aspect, when the reset button 425 is pressed, the 3D map 415 may be displayed in the default orientation without zoom.

The live bronchoscopy window 450 displays live bronchoscopic video images. By looking at the live bronchoscopy window 450, clinicians can steer the bronchoscope 144 to navigate in the luminal network of the lung toward the target. The sensor 143 sticks out of the bronchoscope 144 a predetermined distance. The bronchoscope cannot navigate beyond a predetermined size of airway of the lung due to its size. Before that position, the optical sensor transmits a stream of live bronchoscopic video images to the workstation 120.

Once the bronchoscope 144 becomes wedged in the airway or when the live bronchoscopy 450 does not provide any information, the catheter 142 and sensor 143 may be extended out of the bronchoscope 144 and navigated further through the peripheral branches of the lung toward the target. At this point, once peripheral navigation begins, the endoscopic navigation system 100 and particularly the workstation 120 may automatically switch to a peripheral navigation mode in which the windows presented on the display 122 are changed. For example, since the optical sensor will merely be receiving the same image once the bronchoscope 144 is wedged or when the live bronchoscopy 450 does not provide any information, it may be desirable to switch from a live bronchoscopy window 450 to a virtual bronchoscopy window.

FIG. 4B illustrates a sample peripheral navigation view in accordance with embodiments of the present disclosure. In this configuration, the 3D map window 410 and the live bronchoscopy window 450 of FIG. 4A may be stacked in the left side of the display and a local view window 460 is displayed in the right side. The local view window 460 shows an airway 465 as a black area enclosed by gray-blurred boundaries. A graphical representation 470 of the sensor 143 positioned at the distal tip of the catheter 142 or the LG 145 and a target 475 are also shown in the local view window 460. In an aspect, the target 475 may be displayed as a ball or another shape. The actual size of the target 475 need not synchronized with the local view window 460, thus it may appear full size despite being some distance from the location of the sensor 143. The local view window 460 shows and overlays the target 475, the pathway plan 480, and the sensor 143.

The pathway plan 480 is displayed as a curve from the bottom of the local view window 460 to the target 475 to guide a clinician to reach the target 475. The local view window 460 further displays a distance indicator 485. The distance shown in the distance indicator 485 may be in the International Standard units ("the SI units") or U.S. customary units based on a setting. In FIG. 4B, the distance to the target is shown as 9.2 cm in the SI units. This distance may represent a distance to the target 475 following the pathway plan 480.

Figure 5:
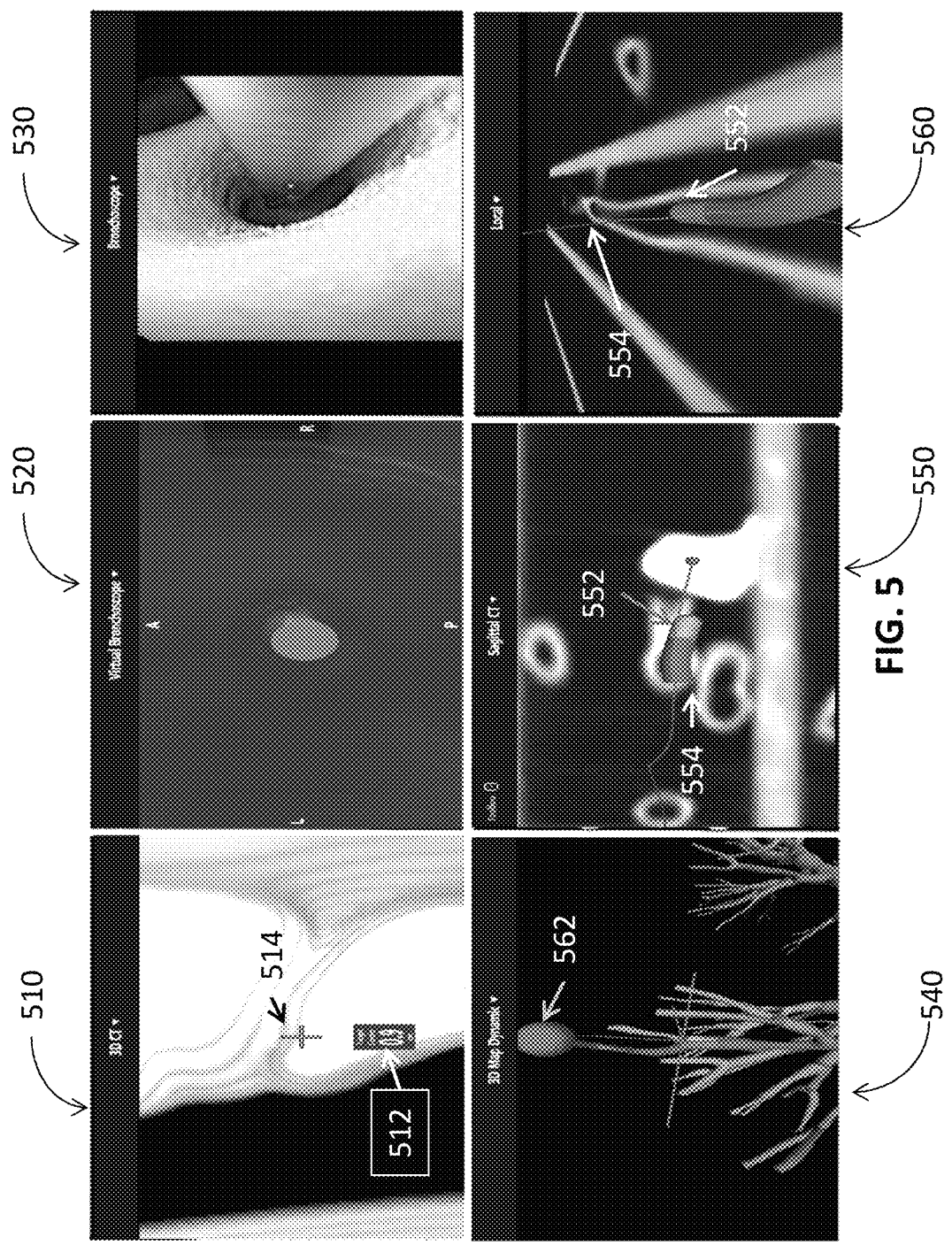

FIG. 5 illustrates six windows for displaying actual navigation to a target in accordance with embodiments of the present disclosure. Six windows are a 3D CT window 510, a virtual bronchoscopy window 520, a live bronchoscopy window 530, a 3D map dynamic window 540, a sagittal view window 550, and a local view window 560. As the graphical representation 522 of the sensor 143 of the LG moves, six windows 510-560 may change correspondingly. Since the bronchoscopy window 530 cannot go further after a certain point of a lung branch, the live bronchoscopy window 530 may show the same image after the certain point. Or, in an aspect, the live bronchoscopy window 530 may be automatically removed from the screen of the display after the sensor 143 passes the certain point.

The 3D CT window 510 may display views directly located in front of the sensor 143 of the LG and show high density structures, such as blood vessels and diseased lesions. As shown in the 3D CT window 510, a distance 512 to the target is displayed. The 3D CT window 510 may also show a next way point 514 in a cross form, which indicates which way the sensor 143 should go to. Descriptions for the virtual bronchoscopy window 520, the bronchoscopy window 530, and the 3D map dynamic window 540 are similar to those above and are omitted.

In an aspect, the target lesion marked on the 3D CT window 510 may be overlaid in a fluoroscopic image to produce a composite image. Since the fluoroscopic images do not show the target lesion, the composite image may be displayed to show a virtual reality in the fluoroscopic image to provide further convenience for the clinicians.

The sagittal view window 550 displays an image in the sagittal plane and overlays a graphical representation 522 of the sensor 143 within the sagittal plane image. The sagittal view window 550 may be switched to the coronal view window or the axial view window based on the direction in which the sensor 143 moves. When the coronal view window is better to show the movement of the sensor 143, the coronal view window automatically replaces the sagittal view window 550. In an aspect, a pathway 554 is also overlaid to the sagittal view window 550.

The local view window 560 displays a slice image (e.g., an axial, coronal, or sagittal image) located at and aligned with the sensor 143 and overlays the slice image, the graphical representation 552 of the sensor 143, the pathway 554, and the target 562.

In a case when two or more slice images are displayed on the screen of the display, the slice images are synchronized based on the location of the sensor 143. In other words, when the sensor 143 moves, the display displays slice images corresponding to the location of the sensor 143. Further, the 3D CT window 510, the virtual bronchoscopy window 520, the 3D map dynamic window 540, and the local view window 560 are also synchronized based on the current position of the sensor 143. When the user of the bronchoscopy pans or zooms, the slice images, the 3D map dynamic window 540, the local view window 560 may also be synchronized. In some instances the virtual bronchoscopy window 520 may not be synchronized with pan and zoom.

In an aspect, the number of windows displayed on the screen may be automatically adjusted based on the procedural mode and the positional information of the sensor 143. Clinicians may also manually remove a window from the screen and add a window to the screen up to, for example, six. The number of windows displayed on the screen, however, may not be limited to a predetermined number but can be increased or decreased based on the real estate of the screen, the mode, and/or a clinician's preference. In an embodiment, clinicians may manually switch the locations of any windows described above, stack them vertically, increase or decrease the size of the windows, and add or remove any windows.

Figure 6:
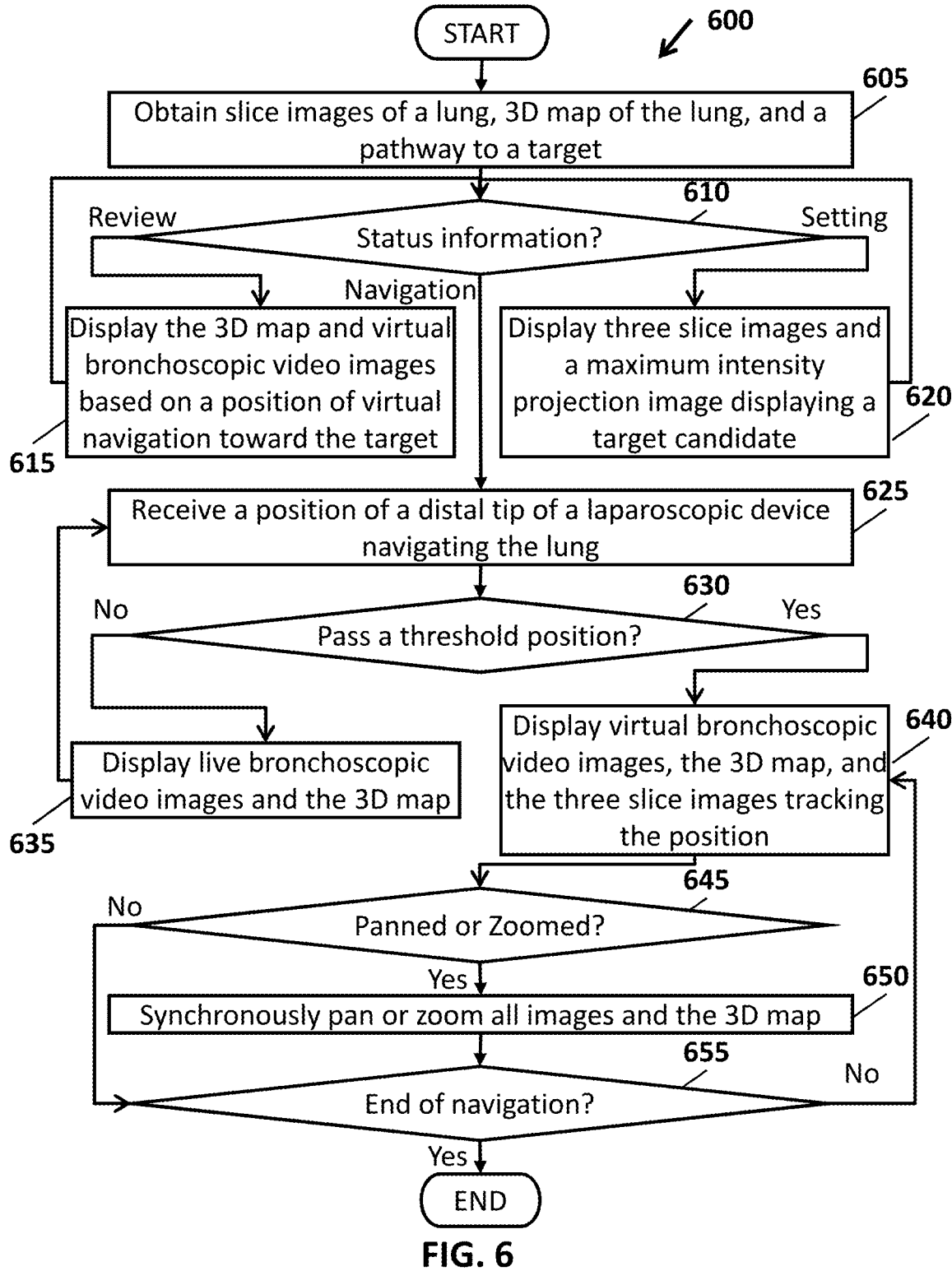
FIG. 6 is a flowchart illustrating a method for dynamically displaying medical images in accordance with embodiments of the present disclosure.

FIG. 6 shows a flowchart illustrating a method 600 for dynamically displaying medical images based on status information and positional information of a navigation instrument 140 in accordance with embodiments of the present disclosure. Workstation 120 obtains DICOM images of a patient (e.g., CT, CAT, ultrasonic images, and so on), and generates a 3D map of the structure imaged (e.g., the lungs).

In step 610, the status information is identified. The status information may indicate the status of the workstation 120. When it is determined that the endoscopic navigation system 100 is in a target management mode, the display 122 may display three 2D images (e.g., sagittal, axial, coronal images) of the imaged lungs and a maximum intensity projection image, all of which show a target candidate, in step 620. By displaying these images, a clinician may easily identify targets, their location and size, and determine a pathway to reach the target. Though such steps are typically undertaken, as described above as a separate process undertaken prior to beginning a navigation procedure, there are instances that during a procedure a clinician may wish to return to a target management mode from a navigation mode.

In practice it is not uncommon that prior to beginning a navigation procedure, but after planning a procedure, a pathway reviewing mode may be entered. In a pathway review, the workstation 120 displays a 3D map and virtual bronchoscopic video images in step 615 and as shown in FIG. 3. In the pathway reviewing mode, the display 122 depicts a virtual navigation to the target and a pathway in, for example, the luminal network of the lung to the target. The display 122 may also display 2D images based on the position of the virtual navigation in the luminal network, where the 2D images are, for example, sagittal, coronal, and axial images. Following completion of the review, the method 600 goes back to step 610 to check the status information.

After the status information determines that a navigation mode has been entered in step 610, positional information is received from the sensor 143 within the EM field generated by the EM field generator 165 in step 625. The positional information identifies a position of the sensor 143 within the EM field, and can be registered to the 2D images and 3D map such that a representation of the distal tip of the catheter 142 is depicted in the 2D images and the 3D map. Initially the sensor 143 is located at the end of the bronchoscope 144. In step 630, it is determined whether the position of the sensor 143 has passed a threshold position. Due to a size of a bronchoscope, the bronchoscope cannot navigate further than the threshold position. The threshold position may be a predetermined position such as the bottom of the trachea, the primary bronchial tree, or any part of a bronchial tree whose diameter is less than a predetermined diameter (e.g., that of the bronchoscope). As such, the bronchoscope becomes wedged in the airways of the lung necessitating advancement of the catheter 142 beyond the distal end of the bronchoscope 144.

In an aspect the threshold position may be a situation where the live bronchoscopic video images do not provide any information and need to be changed to virtual bronchoscopic video images to further navigate through the luminal network of the lung. For example, the threshold position may be a situation where the bronchoscope is obstructed by mucus or bleeding.

Before reaching the threshold, the display 122 may display live bronchoscopic video images and the 3D map in step 635, as shown in FIG. 4A. The live bronchoscopic video images show the bronchoscope 144 following the pathway to the target. In an aspect, the display 122 may also show 2D images of the lung showing the current position of the sensor 143 of the navigation instrument 140 from a desired view (e.g., coronal, sagittal, axial, or another). The method 600 keeps receiving the positional information and displaying the live bronchoscopic video images in steps 625-635 until the sensor 143 passes the threshold position.

When it is determined that the position of the sensor 143 passed the threshold position in step 630, the display 122 changes the images being displayed and may now depict a virtual bronchoscopic video image (e.g., a fly through view similar to that depicted during the reviewing mode but showing the instant location of the sensor 143 in the images), the 3D map, and the three 2D images in step 640. In such an instance the live bronchoscopy window 450 of FIG. 4A is of little value as the catheter 142 and sensor 143 have been extended beyond the image of the optics, and in essence the video image does not change. All the images displayed by the display 122 may synchronously displayed and updated based on the current position of the sensor within the luminal network. In other words, all images track the current position of the sensor 143 in the 3D map and any displayed 2D images.

In an aspect, the mode may further include marker placement mode, biopsy positions tracking/management mode, biopsy helper mode, conclusion/summary mode, etc. Relevant images corresponding to each mode are displayed to facilitate or advance procedures in each mode.

As described above, each image may include a pan or zoom button or slider. In step 645, it is determined whether a pan or zoom feature of one image is performed by a clinician. In addition to the pan and zoom button or slider, pan and zoom features may be activated by an input device such as a keyboard and a mouse, by a touch action (e.g., pinching or double clicking) on the display screen, by a gesture of a clinician monitored by a camera, or by an audible sound. When the pan or zoom is not performed, the method 600 proceeds to step 655. Otherwise, in step 650, the display 122 synchronously pans or zooms all images including the 3D map corresponding to the pan or zoom of the image. In this way, all images may be integrally panned or zoomed. The 3D map window may be switched to the 3D map dynamic window so that the switched 3D map dynamic window can be synchronously panned or zoomed. Images displayed on the display screen may include targets, pathways, waypoints, biopsy markers, organs, or medical instruments.

In step 655, it is determined whether the navigation is ended or whether the navigation instrument 140 reaches the target. If it is not, the method 600 keeps performing steps 640-655 until the sensor 143 of the navigation instrument 140 arrives proximate the target. When the method 600 is ended, a biopsy or treatment procedure may be performed. If an LG has been used, the LG will be removed and replaced by the biopsy or treatment tool within catheter 142, if however, the sensor 143 is integrated within the catheter 142, the biopsy or treatment tools may simply be advanced as required to perform the procedure.

As a result of the methodology described in FIG. 6, the images presented on display 122 can be updated at each phase of a procedure, eliminating the need for a clinician to take their hands off of the navigation instrument 140 or the bronchoscope 144. As will be appreciated by those of skill in the art, the embodiments described above are exemplary and not limiting on the scope of the present disclosure. As a result different groupings of images and 3D maps may be presented at different phase of a procedure. Further, the phases may be optimized or pre-selected by a clinician creating a user selected intelligent display that is customized for the preferences of a particular clinician, hospital, or for a particular type of procedure to a particular portion of the lungs or other area accessed by the devices and systems described herein.

The workstation 120 may be one of a variety of computing systems including, a laptop, desktop, tablet, or other similar device. The display 122 may be touch-sensitive and/or voice-activated, enabling the display 122 to serve as both an input device and an output device. In an aspect, the memory 126 of FIG. 1 may be one or more solid-state storage devices, flash memory chips, mass storages, tape drives, or any computer-readable storage media which are connected to a processor through a storage controller and a system communications bus. Computer readable storage media include non-transitory, volatile, non-volatile, removable, or non-removable media implemented in any method or technology for storing information such as computer-readable instructions, data structures, programs or other data. For example, computer-readable storage media includes random access memory (RAM), read-only memory (ROM), erasable programmable read only memory (EPROM), electrically erasable programmable read only memory (EEPROM), flash memory or other solid state memory technology, CD-ROM, DVD or other optical storage, magnetic cassettes, magnetic tape, magnetic disk storage or other magnetic storage devices, or any other medium which can be used to store desired information and which can be accessed by the display device.

In embodiments, the workstation 120 may further include a separate graphic accelerator that performs only the image-processing functions so that the one or more processors 124 may be available for other programs. The network interface 128 enables other computing devices and/or the imaging devices 110 to communicate with each other through a wired and/or wireless network connection. In FIG. 1, the workstation 120 is shown to transmit or receive medical images, medical data, and control data with the imaging device 110 via a wired connection but data may be transmitted wirelessly.

In an aspect, the memory or storage space may in a network cloud, and the image processing or other processing necessary for planning or performing navigation through the luminal network of the lung may be done by a computing device in the network cloud.

The input device 129 is used for inputting data or control information, such as setting values, text information, and/or controlling the workstation 120. The input device 129 may include a keyboard, mouse, scanning devices, or other data input devices. A system communication bus may connect each other among the display 122, one or more processors 124, the memory 126, the network interface 128, and the input device 129. In an aspect, the input device 129 may further include voice, touch, or gesture.

In another aspect, the slice images of the lung may be obtained by an imaging device using an imaging modality, which may include computed tomographic (CT) technique, radiography, tomogram produced by a computerized axial tomography (CAT) scan, magnetic resonance imaging (MRI), ultrasonography, contrast imaging, fluoroscopy, nuclear scans, and positron emission tomography (PET).

In addition, reference is made to following commonly assigned applications which teach features of image processing and user-interface updating among other features which are relevant to the systems described herein: U.S. Provisional Patent Application Ser. No. 62/020,240 entitled "System And Method For Navigating Within The Lung," filed on Jul. 2, 2014, by Brown et al.; U.S. Provisional Patent Application Ser. No. 62/020,220 entitled "Real-Time Automatic Registration Feedback," filed on Jul. 2, 2014, by Brown et al.; U.S. Provisional Patent Application Ser. No. 62/020,177 entitled "Methods for Marking Biopsy Location," filed on Jul. 2, 2014, by Brown; U.S. Provisional Patent Application Ser. No. 62/020,242 entitled "Unified Coordinate System For Multiple CT Scans Of Patient Lungs," filed on Jul. 2, 2014, by Greenburg; U.S. Provisional Patent Application. No. 62/020,245 entitled "Alignment CT," filed on Jul. 2, 2014, by Klein et al.; U.S. Provisional Patent Application Ser. No. 62/020,250 entitled "Algorithm for Fluoroscopic Pose Estimation," filed on Jul. 2, 2014, by Merlet; U.S. Provisional Patent Application Ser. No. 62/020,253 entitled "Trachea Marking," filed on Jul. 2, 2014, by Lachmanovich et al.; U.S. Provisional Patent Application Ser. No. 62/020,261 entitled "Lung And Pleura Segmentation," filed on Jul. 2, 2014, by Markov et al.; U.S. Provisional Patent Application Ser. No. 62/020,258 entitled "Cone View—A Method Of Providing Distance And Orientation Feedback While Navigating In 3D," filed on Jul. 2, 2014, by Lachmanovich et al.; U.S. Provisional Patent Application Ser. No. 62/020,262 entitled "Dynamic 3D Lung Map View for Tool Navigation Inside the Lung," filed on Jul. 2, 2014, by Weingarten et al.; U.S. Provisional Patent Application Ser. No. 62/020,261 entitled "System and Method for Segmentation of Lung," filed on Jul. 2, 2014, by Markov et al.; and U.S. Provisional Patent Application Ser. No. 62/020,257 entitled "Automatic Detection Of Human Lung Trachea," filed on Jul. 2, 2014, by Markov et al. Further, the present disclosure All of these references are directed to aspects of processing the DICOM images, detecting the trachea, navigating within the lung, and displaying the DICOM images and processed images to provide enhanced clarity and performance for analysis, diagnostic, and treatment systems relating to, among other things, lung treatment planning and navigation. All of these applications are incorporated herein by reference. Although the present disclosure has been described in terms of specific illustrative embodiments, it will be readily apparent to those skilled in this art that various modifications, rearrangements and substitutions may be made without departing from the spirit of the present disclosure. The scope of the present disclosure is defined by the claims appended hereto.

What is claimed is:

1. A medical image display apparatus for displaying medical images of a lung on a screen, comprising:
   a network interface configured to receive positional information from a position sensor disposed on one of a catheter or a navigation instrument disposed within a working channel of the catheter, a live bronchoscopic video stream from an optical sensor of a bronchoscope through which the catheter and the navigation instrument are configured to be inserted for navigation within a patient's lung, and images from an imaging device;
   a memory storing instructions;
   a processor configured to execute the instructions; and
   a display configured to dynamically display windows on the screen,
   wherein the instructions, when executed by the processor, cause the medical image display apparatus to:
   determine endoscopic navigation information of the display, which indicates a mode among a pathway reviewing mode, a target management mode, or a navigation mode; and
   dynamically vary a number of the windows to be displayed on the screen based on a change of the mode indicated by the determined endoscopic navigation information and the positional information, wherein:
   the target management mode includes a first window displayed on the screen presenting a three-dimensional (3D) map of a patient's lung and at least one additional window displayed on the screen that is generated in response to a selection of a target in the 3D map of the patient's lung, the at least one additional window presenting an image of the selected target; and
   the navigation mode further includes:
   a central navigation mode wherein a first window and a second window are displayed on the screen, the first window presenting the 3D map of the patient's lung and a current position indicator displayed on the 3D map representing a current position of the position sensor within the patient's lung, and the second window presenting the live bronchoscopic video stream showing an actual position of the position sensor within the patient's lung, wherein the current position indicator moves relative to the 3D map displayed on the screen as the position sensor is navigated within the patient's lung such that a position of the current position indicator displayed on the 3D map is synchronized with the actual position of the position sensor shown in the live bronchoscopic video stream; and
   a peripheral navigation mode wherein a third window presenting a virtual bronchoscopic video stream is caused to be displayed on the screen with the first and second windows in response to the positional information indicating that the position sensor is advancing distally from a distal end of the bronchoscope toward the target and past a threshold position within a bronchus of the patient, the virtual bronchoscopic video stream including graphical representations of the position sensor, the target, and a planned pathway to the target to depict the position sensor advancing distally to the distal end of the bronchoscope past the threshold position and along the planned pathway toward the target.

2. The medical image display apparatus according to claim 1, wherein the image of the selected target is selected from the group consisting of a sagittal image, a coronal image, and an axial image.

3. The medical image display apparatus according to claim 2, wherein the sagittal, coronal, or axial image is captured by computed tomography, fluoroscopy, computer aided tomography, positron emission tomography, or magnetic resonance imaging.

4. The medical image display apparatus according to claim 1, wherein changes in the positional information indicate movements of the position sensor in the patient's lung.

5. The medical image display apparatus according to claim 1, wherein the at least one additional window of the target management mode comprises a first window presenting an axial image of the selected target, a second window presenting a coronal image of the selected target, and a third window presenting a sagittal image of the selected target.

6. The medical image display apparatus according to claim 1, wherein the 3D map is displayed with an orientation indicator.

7. The medical image display apparatus according to claim 6, wherein the orientation indicator shows an orientation of the 3D map.

8. The medical image display apparatus according to claim 1, wherein the display automatically orients the 3D map to show a current position of the position sensor in the 3D map.

9. A medical image display system comprising:
   a catheter configured to be received through a working channel of a bronchoscope;
   a navigation instrument configured to be received through the catheter and to navigate inside of a patient, at least one of the catheter or the navigation instrument having a position sensor configured to transmit positional information; and
   a medical image display apparatus comprising:
   a network interface configured to receive the positional information and a live bronchoscopic video stream from the bronchoscope;
   a processor configured to execute instructions;
   a memory storing the instructions; and a display configured to display windows on a screen, wherein the instructions, when executed by the processor, cause the medical image display apparatus to:

dynamically vary a number of the windows to be displayed on the screen based on a change of a mode of operation of the medical image display apparatus;

operate in a target management mode to display a first window on the screen presenting a three-dimensional (3D) map of the patient's lung and at least one additional window on the screen that is generated in response to a selection of a target in the 3D map of the patient's lung, the at least one additional window presenting an image of the selected target;

operate in a central navigation mode to display a first window and a second window, the first window presenting the 3D map of the patient's lung and a current position indicator displayed on the 3D map representing a current position of the position sensor within the patient's lung, and the second window presenting the live bronchoscopic video stream showing an actual position of the position sensor within the patient's lung, wherein the current position indicator moves relative to the presented 3D map as the position sensor is navigated within the patient's lung such that a position of the current position indicator displayed on the 3D map is synchronized with the actual position of the position sensor shown in the live bronchoscopic video stream; and operate in a peripheral navigation mode wherein a third window presenting a virtual bronchoscopic video stream is caused to be displayed on the screen with the first and second windows in response to the positional information indicating that the position sensor is advancing toward the target past a threshold position within the patient's lung, the virtual bronchoscopic video stream including graphical representations of the position sensor, the target, and a planned pathway to the target to depict the position sensor advancing distally past the threshold position and along the planned pathway toward the target.

10. The medical image display system according to claim 9, wherein the at least one additional window of the target management mode comprises a first window presenting an axial image of the selected target, a second window presenting a coronal image of the selected target, and a third window presenting a sagittal image of the selected target.

* * * * *